United States Patent [19]

Vinick

[11] 4,238,392

[45] Dec. 9, 1980

[54] PURIFICATION OF L-ASPARTYL-L-PHENYLALANINE ALKYL ESTERS

[75] Inventor: Fredric J. Vinick, Waterford, Conn.

[73] Assignee: Pfizer Inc., New York, N.Y.

[21] Appl. No.: 89,640

[22] Filed: Oct. 29, 1979

[51] Int. Cl.³ ............................................. C07C 103/52
[52] U.S. Cl. ............................................... 260/112.5 R
[58] Field of Search ................................. 260/112.5 R

[56] References Cited

U.S. PATENT DOCUMENTS

| | | | |
|---|---|---|---|
| 3,798,207 | 3/1974 | Ariyoshi et al. | 260/112.5 R |
| 4,031,258 | 6/1977 | Haas et al. | 260/112.5 R |
| 4,173,562 | 11/1979 | Bachman et al. | 260/112.5 R |

Primary Examiner—Delbert R. Phillips
Attorney, Agent, or Firm—Francis X. Murphy; Charles J. Knuth; Peter C. Richardson

[57] ABSTRACT

L-Aspartyl-L-phenylalanine alkyl esters prepared by the reaction of L-aspartic acid N-thiocarboxyanhydride and an appropriate L-phenylalanyl alkyl ester are deodorized by contacting the L-aspartyl-L-phenylalanine alkyl ester in aqueous solution with an effective amount of an alkali metal periodate.

9 Claims, No Drawings

PURIFICATION OF L-ASPARTYL-L-PHENYLALANINE ALKYL ESTERS

BACKGROUND OF THE INVENTION

This invention relates to the deodorization and purification of L-aspartyl-L-phenylalanine alkyl esters. L-Aspartyl-L-phenylalanine alkyl esters, having from 1 to 3 carbon atoms in the alkyl group, especially the methyl ester, are useful as sweetening agents. One desirable method for preparing such esters is by the reaction of L-aspartic acid N-thiocarboxyanhydride and an appropriate L-phenylalanine alkyl ester in aqueous solution, for example, in accord with the general procedures described in J. Org. Chem. 36, 49 (1971). However, this method suffers from the disadvantage that small amounts of certain impurities are formed in this reaction by undesired side reactions or degradation of species in the reaction mixture, which impart an unpleasant odor to the L-aspartyl-L-phenylalanine alkyl ester produced. Such odorous impurities are not removed in conventional procedures for the recovery and purification of the desired ester, such as recrystallization or the removal of amino acid impurities by chromatographic methods, and are present in the otherwise purified crystalline product. The unpleasant odor associated with the presence of these impurities is particularly undesirable in view of the intended use of the L-aspartyl-L-phenylalanine alkyl esters as sweetening agents for foodstuffs and beverages and development of a commercially acceptable sweetening agent for such use requires removal of the undesired malodorous impurities. Such impurities may also adversely affect the taste quality of products containing these sweetening agents.

SUMMARY OF THE INVENTION

In accord with the present invention, odorous impurity-containing L-aspartyl-L-phenylalanine alkyl esters are deodorized by reaction with an alkali metal periodate in aqueous solution. More particularly, the present invention provides a process for deodorizing an L-aspartyl-L-phenylalanine alkyl ester having odorous impurities formed in the preparation of the ester by the reaction of L-aspartic acid N-thiocarboxyanhydride and an L-phenylalanine alkyl ester, the alkyl groups having from 1 to 3 carbon atoms, comprising contacting the L-aspartyl-L-phenylalanine alkyl ester in aqueous solution at a pH from about 2 to 6, preferably from about 4.5 to 6, with an effective amount of an alkali metal periodate to a temperature from about 0° to 50° C., preferably 10° to 25° C. Preferably, an activated charcoal in an amount of about 1 to 25 weight percent, based on the amount of L-aspartyl-L-phenylalanine alkyl ester, is also added to the reaction solution. If desired, an alkali metal chlorate is added to the reaction solution in an amount sufficient to provide a chlorate:periodate ratio of 1:1 to 20:1, preferably 1:1 to 10:1. The process of this invention is of particular interest for the deodorization and purification of L-aspartyl-L-phenylalanine methyl ester.

DETAILED DESCRIPTION OF THE INVENTION

L-Aspartyl-L-phenylalanine alkyl esters are readily prepared by the reaction of L-aspartic acid N-thiocarboxyanhydride and an appropriate L-phenylalanine alkyl ester having from 1 to 3 carbon atoms in the alkyl group, in accord with the following reaction scheme:

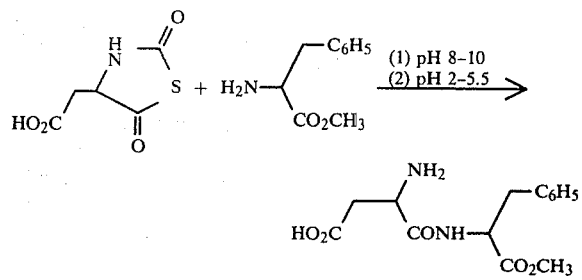

The L-aspartic acid N-thiocarboxyanhydride is prepared by methods known in the art, for example, as described in J. Org. Chem. 36, 49 (1971), for example, by the reaction of an N-alkoxy thiocarbonyl-L-aspartic acid with a phosphorous trihalide in a lower alkyl acetate solvent as described in copending U.S. patent application Ser. No. 89,641, filed concurrently herewith. The L-phenylalanine alkyl esters are commercially available, or may be readily prepared by heating L-phenylalanine and the appropriate alkyl alcohol in the presence of a catalytic amount of a mineral acid, such as hydrochloric acid.

The reaction of the L-aspartic acid N-thiocarboxy anhydride and L-phenylalanine alkyl ester is conducted in aqueous solution at a pH from about 8 to 10, preferably about 9, and a temperature between about −10° C. and 40° C., preferably from about 0° to 10° C. If desired, inert organic co-solvents, such as an alkyl alcohol of 1 to 3 carbon atoms, an ether such as dioxane or tetrahydrofuran, and the like may be added. The intermediate N-thiocarboxyamino dipeptide formed in this reaction is then converted to the desired L-aspartyl-L-phenylalanine alkyl ester by adjusting the pH of the reaction solution to between about 2 and 6. At pH values close to the isoelectric point, from about 4.5 to 5.5, the L-aspartyl-L-phenylalanine alkyl ester precipitates from solution and may be collected, for example, by filtration.

In the above described reaction to form the desired L-aspartyl-L-phenylalanine alkyl ester, undesirable odorous impurities are formed in small amounts as a result of undesired side reactions or by degradation of amino-acid and peptide derivatives present in the reaction solution. While the identity of the odorous impurities has not been established, such impurities have been found to be consistently formed in the reaction of L-aspartic acid N-thiocarboxyanhydride and an L-phenylalanine alkyl ester and the present process provides a means of deodorizing the esters, regardless of the precise chemical structure of the odorous impurities, and to provide L-aspartyl-L-phenylalanine alkyl esters in a purified form suitable for use in commercial sweetening products. Similarly, the mechanism of the deodorization has not been established and the present invention is not to be construed as being limited to any particular mechanism of reaction between the undesired odorous impurities and the alkali metal periodate.

The undesired odors associated with impurities formed in the reaction of the L-aspartyl-N-thiocarboxyanhydride and the L-phenylalanine alkyl ester are removed by the process of the present invention by contacting an aqueous solution of the desired ester with an alkali metal periodate. It will be understood that, in one embodiment of the present process, the alkali metal periodate may be added to the reaction mixture resulting from the reaction of L-aspartic acid N-thiocarboxyanhydride and the L-phenylalanine alkyl ester followed by acidification and containing the crude desired ester, i.e. before isolating the ester from the reaction solution. Alternatively, the desired L-aspartyl-phenylalanine alkyl ester can be isolated from the initial reaction mixture and then redissolved in aqueous solution, to which the alkali metal periodate is then added. These methods of practicing the present invention and other methods which will be obvious to those skilled in the art are within the scope of this invention as described in the specification and claims hereof.

If desired, the aqueous solution may contain organic co-solvents such as alkyl alcohols of 1 to 3 carbon atoms, ethers such as dioxane or tetrahydrofuran, and the like.

The alkali metal periodate is preferably sodium or potassium metaperiodate. An effective amount of the alkali metal periodate for removal of the odorous impurities is typically from about 0.1 mole percent to about 20 mole percent, preferably about 0.5 to about 5 mole percent, based on the L-aspartyl-L-phenylalanine alkyl ester present in solution. If desired, the alkali metal periodate can be formed in situ by adding an alkali metal iodate, such as potassium or sodium iodate, together with an oxidizing agent, such as an alkali metal chlorate, for example sodium or potassium chlorate. The use of alkali metal iodates and oxidizing agents to form the alkali metal periodate in situ in this manner is intended to be within the scope of the present invention and of the claims hereof.

If desired, an alkali metal chlorate, preferably sodium or potassium chlorate, may also be added to the reaction solution containing the alkali metal periodate in an amount sufficient to provide a chlorate:periodate ratio of about 1:1 to 20:1, preferably 1:1 to 10:1. The alkali metal chlorate acts to regenerate periodate reduced in the reaction, thereby facilitating removal of the undesired impurities and providing economy of operation.

In a preferred procedure, it has been found that deodorization of the L-aspartyl-L-phenylalanine alkyl ester-containing reaction solution is facilitated by the addition to the solution of a solid adsorbant. A particularly preferred solid adsorbant is activated carbon, generally employed in an amount of about 1 to 25 wt. %, preferably about 5 to 15 wt. %, based on the L-aspartyl-L-phenylalanine alkyl ester in solution. Other adsorbants, such as diatomaceous earth, silica gels and the like may also be employed.

The reaction is conducted in aqueous solution, optionally containing organic co-solvents, as described above, at a pH from about 2 to 6, preferably from about 4 to 6. The solubility of the L-aspartyl-L-phenylalanine alkyl esters is greatest at pH values between about 2 and 4. Accordingly, when conducting the reaction at pH values from about 4 to 6, sufficient solvent should be added to ensure that the ester is dissolved. The deodorization process is generally conducted at a temperature from about 0° to 50° C., preferably from about 10° to 25° C. The reaction is continued until no odor can be detected. Reaction times will vary depending on the reaction temperature, the amount of periodate added, the concentration of impurities and other factors, but will generally be from about 2 to 24 hours.

The desired L-aspartyl-L-phenylalanine alkyl esters deodorized as described above to contain no detectable odorous impurities may be recovered from the aqueous solution by adjusting the pH, if necessary, to about 4.5 to 5.5, preferably about 5 to 5.2, and concentrating the solution, for example under vacuum, such that the desired ester precipitates from solution.

The present invention is illustrated by the following examples. However, it should be understood that this invention is not limited to the specific details of these examples.

EXAMPLE 1

L-Aspartic acid (571 g, 4.29 mol) was added gradually with stirring to 350.9 g (8.58 mol) of 50% sodium hydroxide solution at 0° C. Methyl methyl xanthate (550 g, 4.51 mol) in 405 ml of methanol was then added as rapidly as possible. The mixture was heated at 45° C. for 1.5 hrs, cooled to room temperature, and washed with two portions of methylene chloride. The methylene chloride washes were discarded and the aqueous phase acidified with concentrated hydrochloric acid at 0° C. The solution was extracted with three portions of ethyl acetate, and the combined extracts washed with brine and dried over anhydrous magnesium sulfate. The solvent was evaporated in vacuo to give a yellow oil which crystallized upon addition of ethylene dichloride and n-hexane. The N-methoxythiocarbonyl-L-aspartic acid was collected by filtration, washed with fresh n-hexane, and dried (420 g, 47%).

mp 128°–130° C.

nmr (DMSO-$d_6$) δ2.73 (d, 2H, J=6 Hz), 3.63 (s, 3H), 4.43 (dt, 1H, J=6 Hz, 8 Hz), 6.63 (d, 1H, J=8 Hz).

ir (KBr) 1715, 1515 cm$^{-1}$.

N-Methoxythiocarbonyl-L-aspartic acid (207.0 g, 1.00 mol) was dissolved in 1200 ml ethyl acetate at 0° C., and phosphorous tribromide (47 ml, 0.50 mol) was added in one portion. The cooling bath was removed and the solution was stirred for 10 minutes after which time a granular white precipitate had formed. The reaction mixture was cooled to 0°–5°, and the product collected by filtration, washed with a small volume of ether, and dried. The yield of analytically pure L-aspartic acid N-thiocarboxyanhydride was 157.4 g (90%).

mp 200°–205° C. (dec.).

$[\alpha]_D^{25} = -109.5°$ (C=1, THF).

ir (KBr) 3225, 1739, 1724, 1653, 1399 cm$^{-1}$.

nmr (DMSO-$d_6$) δ2.83 (d, 2H, J=5 Hz), 4.70 (t, 1H, J=5 Hz).

L-Phenylalanine methyl ester hydrochloride (108 g, 0.50 mol) was dissolved in 1000 ml water at 0°–5° C. and the pH of the solution adjusted to 9.0 with 50% sodium hydroxide solution. L-Aspartic acid N-thiocarboxyanhydride (91.9 g, 0.525 mol) was then added in portions with vigorous stirring; the pH was maintained at 8.9–9.1 by the addition of 50% sodium hydroxide solution as needed. Stirring and addition of hydroxide was continued until the pH stabilized at 9.0 (ca 60 min). The pH was then adjusted to 5.0–5.5 with 12 N hydrochloric acid. Sufficient methanol was added to facilitate good stirring. The precipitated L-aspartyl-L-phenylalanine methyl ester was collected by filtration, washed with a small quantity of ice water, and dried. The isolated yield of crude product was 92 g (63%).

The L-aspartyl-L-phenylalanine methyl ester had an unpleasant odor.

EXAMPLE 2

Crude, odorous L-aspartyl-L-phenylalanine methyl ester (1.00 g, 3.4 mmol) prepared from L-aspartic acid N-thiocarboxyanhydride was dissolved in 100 ml of water at 25° C. To this solution were added 100 mg of activated carbon (DARCO G-60, 10 wt %) and 15 mg of sodium metaperiodate (0.68 mmol, 2 mol %). The mixture was stirred at 25° C. for 16 hours, filtered, concentrated in vacuo, and diluted with isopropanol. Pure crystalline L-aspartyl-L-phenylalanine methyl ester was collected by filtration, washed with ethyl ether, and dried (0.81 g, 81%). This material was found to be completely free of odor, even after prolonged storage in a closed vial.

EXAMPLE 3

Crude, odorous L-aspartyl-L-phenylalanine methyl ester (28.4 g, 96.9 mmol) prepared from L-aspartic acid N-thiocarboxyanhydride was slurried in 250 ml of water at 0° C. 6 N Hydrochloric acid was added until pH 2.2 was achieved; 3.0 g of activated carbon (DARCO G-60, 10 wt %) and 0.65 g of sodium metaperiodate (3 mmol, 3 mol %) were then added. The mixture was stirred at 25° C. for 16 hours, filtered and the pH readjusted to 5.0 with aqueous sodium hydroxide solution. The solution volume was reduced to 150 ml of water and the mixture chilled at 0°–5° C. overnight. Odor-free L-aspartyl-L-phenylalanine methyl ester was collected by filtration, washed with a small quantity of ice water, and dried (17.0 g, 60%).

mp 236°–237° C. (dec.).

$[\alpha]_D^{25} = +31.2$ (C=1, glacial acetic acid).

EXAMPLE 4

Crude, odorous L-aspartyl-L-phenylalanine methyl ester (2.00 g, 6.8 mmol) prepared from L-aspartic acid N-thiocarboxyanhydride was dissolved in 200 ml of water at 25° C. To this solution were added 0.20 g of activated carbon (DARCO G-60, 10 wt %), 7 mg of sodium metaperiodate (0.034 mmol, 0.5 mol %) and 29 mg of sodium chlorate (0.27 mmol, 4 mol %). The mixture was stirred at 25° C. for 16 hours, filtered, concentrated in vacuo to a wet solid, and diluted with isopropanol. Pure, completely odor-free L-aspartyl-L-phenylalanine methyl ester was collected by filtration (two crops), washed with ethyl ether and dried (1.09 g, 54%).

EXAMPLE 5

Crude, odorous L-aspartyl-L-phenylalanine methyl ester (2.00 g, 6.8 mmol) prepared from L-aspartic acid N-thiocarboxyanhydride was slurried in 17 ml of water at 0° C. 12 N Hydrochloric acid was added until pH 2.2 was achieved; 0.20 g activated carbon (DARCO G-60, 10 wt %), 7 mg sodium metaperiodate (0.034 mmol, 5 mol %), and 29 mg sodium chlorate (0.27 mmol, 4 mol %) were then added. The mixture was stirred at 25° C. for 16 hours, filtered, and the pH readjusted to 5.0 with aqueous sodium hydroxide solution. The mixture was concentrated in vacuo to give a wet solid and diluted with isopropanol. Odor-free L-aspartyl-L-phenylalanine methyl ester was collected by filtration (two crops), washed with ethyl ether, and dried (0.01 g, 51%).

EXAMPLE 6

Crude, odorous L-aspartyl-L-phenylalanine methyl ester (2.00 g, 6.8 mmol) prepared from L-aspartic acid N-thiocarboxyanhydride was dissolved in 400 ml of water at 0°–5° C. To this solution were added 0.20 g of activated carbon (DARCO G-60, 10 wt %), 7 mg of sodium metaperiodate (0.034 mmol, 0.5 mol %) and 29 mg of sodium chlorate (0.27 mmol, 4 mol %). The mixture was stirred at 0°–5° C. for 16 hours, filtered, concentrated in vacuo to a wet solid, and diluted with isopropanol. Completely odor-free L-aspartyl-L-phenylalanine methyl ester was collected by filtration (two crops), washed with ethyl ether, and dried (1.03 g, 52%).

EXAMPLE 7

Following the procedure of Example 3, L-aspartyl-L-phenylalanine methyl ester (3.0 g, 10.2 mmol) in 100 ml of water was reacted for 3 hours at 50° C. with sodium iodate (80.7 mg, 0.41 mmol) and sodium chlorate (43.4 mg, 0.41 mmol) in the presence of activated carbon (DARCO G-60) (300 mg). Odor-free L-aspartyl-L-phenylalanine methyl ester was recovered in 63% yield.

EXAMPLE 8

L-Phenylalanine methyl ester hydrochloride (10.8 g, 50 mmol) was dissolved in 90 ml water at 0°–5° C. and the pH of the solution adjusted to 9.0 with 50% sodium hydroxide solution. L-Aspartic acid N-thiocarboxyanhydride (9.19 g, 52.2 mmol) was then added in portions with vigorous stirring; the pH was maintained at 8.9–9.1 by the addition of 50% sodium hydroxide solution as needed. After completion of the addition, stirring was continued until the pH stabilized at 9.0 (ca. 30 min). The pH was then adjusted at 0° C. to 2.0–2.2 and sodium metaperiodate (0.33 g, 1.5 mmol) and activated charcoal (1.50 g) were added. The mixture was stirred for 16 hours at 20° C., filtered, and adjusted to pH 5.0 with 6 N sodium hydroxide at 0° C. The precipitated, odor-free L-aspartyl-L-phenylalanine methyl ester was collected by filtration, washed with a small quantity of ice water, and dried. The isolated yield of product was 11.20 g (76%).

I claim:

1. A process for deodorizing an L-aspartyl-L-phenylalanine alkyl ester having odorous impurities formed in the preparation of said ester by the reaction of L-aspartic acid N-thiocarboxyanhydride and a L-phenylalanine alkyl ester, said alkyl groups having from 1 to 3 carbon atoms, comprising contacting said L-aspartyl-L-phenylalanine alkyl ester in aqueous solution at a pH between about 2 and 6 with an effective amount of an alkali metal periodate at a temperature between about 0° and 50° C.

2. A process according to claim 1, wherein the temperature is between about 10° and 25° C.

3. A process according to claim 1 wherein the pH is between about 4.5 and 6.

4. A process according to claim 1 wherein said alkali metal periodate is sodium periodate.

5. A process according to claim 4 wherein between about 0.5 to 5 mole percent of sodium periodate is employed.

6. A process according to claim 1 wherein said solution additionally contains about 1 to 25 wt. % of an activated carbon.

7. A process according to claim 1 wherein said solution additionally contains an alkali metal chlorate selected from sodium chlorate and potassium chlorate in an amount to provide a chlorate: periodate ratio of 1:1 to 10:1.

8. A process according to claim 1 wherein said ester is L-aspartyl-L-phenylalanine methyl ester.

9. A process according to claim 8 wherein the temperature is between about 10° and 25° C., the pH is between about 4.5 and 6 and the solution additionally contains between 5 and 15% of an activated carbon.

* * * * *